(12) United States Patent
Shue et al.

(10) Patent No.: US 7,771,394 B2
(45) Date of Patent: Aug. 10, 2010

(54) INTRAVENOUS CATHETER INTRODUCING DEVICE

(76) Inventors: Ming-Jeng Shue, No. 14, Lane 8, Chung-I St., Hsi Dist., Taichung City (TW); Phillip Shue, No. 14, Lane 8, Chung-I St., Hsi Dist., Taichung City (TW); Deborah Huang, 7F, No. 5, Sec. 3, Liu-Chun E. Rd., Chung Dist., Taichung City (TW)

( * ) Notice: Subject to any disclaimer, the term of this patent is extended or adjusted under 35 U.S.C. 154(b) by 641 days.

(21) Appl. No.: 11/652,281

(22) Filed: Jan. 10, 2007

(65) Prior Publication Data

US 2008/0125717 A1     May 29, 2008

(30) Foreign Application Priority Data

Jun. 16, 2006   (TW) ............................. 95121678 A

(51) Int. Cl.
*A61M 5/178*   (2006.01)
(52) U.S. Cl. ............................ 604/164.12; 604/164.01; 604/110; 604/168.01
(58) Field of Classification Search ............ 604/164.01, 604/164.06, 164.07, 164.12, 168.01, 110
See application file for complete search history.

(56) References Cited

U.S. PATENT DOCUMENTS

| | | | |
|---|---|---|---|
| 2,705,494 A | | 4/1955 | Broadwin |
| 4,556,060 A | | 12/1985 | Perlin |
| 4,776,346 A | | 10/1988 | Beraha et al. |
| 4,998,924 A | | 3/1991 | Ranford |
| 5,026,346 A | * | 6/1991 | Spanner et al. ............. 604/110 |
| 5,092,851 A | | 3/1992 | Ragner |
| 5,176,656 A | | 1/1993 | Bayless |
| 5,180,370 A | * | 1/1993 | Gillespie .................... 604/110 |

(Continued)

FOREIGN PATENT DOCUMENTS

EP       0812610 A2    12/1997

(Continued)

OTHER PUBLICATIONS

Office Action dated May 8, 2009 from U.S. Appl. No. 11/974,943, 12 pages.

(Continued)

*Primary Examiner*—Nicholas D Lucchesi
*Assistant Examiner*—Leah Stohr
(74) *Attorney, Agent, or Firm*—Alan Kamrath; Kamrath & Associates PA

(57) ABSTRACT

An intravenous catheter introducing device includes a barrel, a tubular grip member disposed to hold a needle seat in a position of use so as to permit a tip end of a needle cannula to extend forwardly of the barrel, a tubular plunger which is movable along a passage of the barrel, and a tubular receptacle which is retained in an accommodation compartment of the tubular plunger and which has socket and air-permeable ends and a flashback chamber. When the plunger is pressed forwardly to permit engagement of the socket end with a rear plug portion of the needle seat and to release the grip member from the barrel, a rearward movement of the needle seat by virtue of a biasing force of a biasing member will force the receptacle to move rearwardly so as to retract the needle cannula into the passage.

11 Claims, 18 Drawing Sheets

U.S. PATENT DOCUMENTS

| | | |
|---|---|---|
| 5,318,538 A | 6/1994 | Martin |
| 5,360,405 A | 11/1994 | Yoon |
| 5,464,418 A | 11/1995 | Schraga |
| 5,575,777 A | 11/1996 | Cover et al. |
| 5,685,855 A | 11/1997 | Erskine |
| 5,704,911 A | 1/1998 | Parsons |
| 5,779,679 A | 7/1998 | Shaw |
| 5,817,058 A * | 10/1998 | Shaw ............... 604/110 |
| 5,865,806 A | 2/1999 | Howell |
| 5,873,856 A | 2/1999 | Hjertman et al. |
| 5,911,705 A | 6/1999 | Howell |
| 6,039,713 A | 3/2000 | Botich et al. |
| 6,210,371 B1 | 4/2001 | Shaw |
| 6,679,864 B2 | 1/2004 | Gagnieux et al. |
| 6,846,301 B2 * | 1/2005 | Smith et al. ............ 604/110 |
| 6,981,965 B2 | 1/2006 | Luther et al. |
| 2001/0037089 A1 | 11/2001 | Domici |
| 2004/0116864 A1 | 6/2004 | Boudreaux |
| 2005/0101917 A1 | 5/2005 | Doyle |
| 2005/0228345 A1 | 10/2005 | Yang et al. |
| 2005/0267416 A1 | 12/2005 | Mohammed |
| 2006/0229563 A1 | 10/2006 | O'Reagan et al. |

FOREIGN PATENT DOCUMENTS

| | | |
|---|---|---|
| EP | 1457229 A1 | 9/2004 |
| EP | 1514568 A1 | 3/2005 |
| EP | 1611916 A1 | 1/2006 |

OTHER PUBLICATIONS

Office Action dated Aug. 6, 2009 from U.S. Appl. No. 11/904,502, 14 pages.

* cited by examiner

INTRAVENOUS CATHETER INTRODUCING DEVICE

CROSS-REFERENCE TO RELATED APPLICATION

This application claims priority of Taiwanese Application No. 095121678, filed on Jun. 16, 2006, the disclosure of which is incorporated herein by reference.

BACKGROUND OF THE INVENTION

1. Field of the Invention

This invention relates to an intravenous catheter introducing device, more particularly to an intravenous catheter introducing device with a needle cannula which is retractable into a tubular plunger for safe disposal.

2. Description of the Related Art

Intravenous catheter introducing devices are generally used to administer a medication fluid into or to draw blood from a patient's vein. Referring to FIG. 1, a conventional intravenous catheter introducing device 9 is shown to include a tubular needle seat 91 with a hub end 911, a needle cannula 94 secured to the hub end 911, a catheter hub 92 sleeved on the needle seat 91, and a flexible tubular catheter 93 secured to the catheter hub 92. In use, the catheter 93 and the needle cannula 94 are inserted into the patient's vein by a health care worker by piercing the patient's vein with a sharp tip of the needle cannula 94 which projects outwardly of the catheter 93. The health care worker then withdraws the needle cannula 94 from the catheter 93 with one hand and, at the same time, applies pressure to the patient's skin with the other hand, thereby leaving the catheter 93 in the patient's vein. Subsequently, a transfusion member (not shown) with the medication fluid or an empty barrel is connected to the catheter hub 92 for administering the medication fluid into the patient's vein or for drawing blood. At this time, the exposed sharp tip of the used needle cannula 94 may create a danger of an accidental needle stick.

Moreover, the conventional intravenous catheter introducing device 9 is specifically not suitable for patients whose blood pressure is not sufficient to permit flow of blood therethrough, such as an emergency case, aged people, and pediatrics patients, and patients whose target vein is barely visible due to abundant adipose tissue, such as women and obese patients, since the health care worker will have difficulty determining whether the catheter 93 has been successfully introduced into the target vein, and may need to locate the vein by moving the needle cannula 94 in the skin of the patient, thereby complicating and prolonging the cannulation procedure and causing great discomfort to the patient.

Furthermore, although conventional self-retracting IV catheter introducers permit self-retraction of the used needle cannula into the syringe barrel after introduction of the catheter is completed, the blood in the barrel may be forced out of the barrel during the retraction of the used needle cannula so that blood contamination may occur.

SUMMARY OF THE INVENTION

One object of the present invention is to provide an intravenous catheter introducing device which can be operated easily and safely to retract a used needle cannula with one hand, and which can prevent the blood from being forced out thereof.

Another object of the present invention is to provide an intravenous catheter introducing device which can facilitate flowing of the blood into the needle cannula to thereby enable the operator to conveniently observe and check the introduction of a catheter.

According to this invention, the intravenous catheter introducing device includes:

a needle cannula which has a front segment terminating at a tip end, and a rear connecting end opposite to the front segment along the axis in a longitudinal direction;

a tubular needle seat which includes a front hub portion that extends along the axis to terminate at a front end, and that is disposed to fix the rear connecting end therein, a gripped portion that extends from the front hub portion away from the front end, and a rear plug portion that extends from the gripped portion and distal from the front hub portion, and that has an internal duct extending through the gripped portion to be communicated with the rear connecting end;

a barrel which has an inner surrounding barrel surface defining a passage therein, the passage having rearward and forward openings, the inner surrounding barrel surface including a larger-diameter portion and a smaller-diameter portion which are disposed proximate to the rearward and forward openings, respectively, the larger-diameter portion having a retaining area which is spaced apart from the smaller-diameter portion in the longitudinal direction;

a tubular grip member which, in a position of use, is disposed to hold, with a holding force, the gripped portion in a position of immovability along the axis relative to the retaining area;

a tubular plunger which is disposed to be movable in the passage along the larger-diameter portion, the plunger having a front opened end wall which is movable to abut against the grip member so as to place the tubular plunger in a pre-disposal position, a rear end wall which is disposed opposite to the front opened end wall, and which extends outwardly of the rearward opening so as to be manually operable, and an intermediate surrounding wall which is interposed between the front opened end wall and the rear end wall, and which defines an accommodation compartment;

a tubular receptacle which has a socket end, an air-permeable end, and a tubular wall segment interposed therebetween to confine a flashback chamber, wherein when the tubular grip member is in the position of use, the tubular receptacle is retained in the accommodation compartment by a first friction force, with the socket end and the air-permeable end respectively confronting the rear plug portion and the rear end wall to establish air communication between the internal duct and the flashback chamber, such that when the tubular plunger is in the pre-disposal position, the socket end is engaged with the rear plug portion, such that when the grip member is pushed forward by virtue of a forward movement of the front opened end wall against the holding force, the gripped portion is released from the grip member so as to permit axial movement of the gripped portion relative to the retaining area, and such that when the gripped portion is released from the grip member, a continued forward movement of the front opened end wall against the first friction force will result in movement of the tubular needle seat together with the tubular receptacle, through the engagement of the rear plug portion with the socket end, towards the rear end wall by virtue of a biasing force so as to place the tubular needle seat and the needle cannula in a disposal position, where the tip end of the needle cannula is retracted into the passage, and where the socket end is closer to the rear end wall than in the position of use;

a biasing member disposed to provide the biasing force;

a catheter hub which defines therein a duct that permits extension of the front segment of the needle cannula therethrough; and a tubular catheter having a proximate segment which is inserted into the duct, and a distal segment which extends from the proximate segment and which surrounds and sheathes the front segment of the needle cannula while permitting the tip end to project forwardly of the distal segment for piercing a patient's skin.

Preferably, an air-permeable member which is made from a porous material is integrally formed with the air-permeable end so as to prevent blood from trickling out of the flashback chamber.

Preferably, the tubular plunger has an outlet which permits air communication between the accommodation compartment and the ambient air, and which is disposed downstream of the air permeable end.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
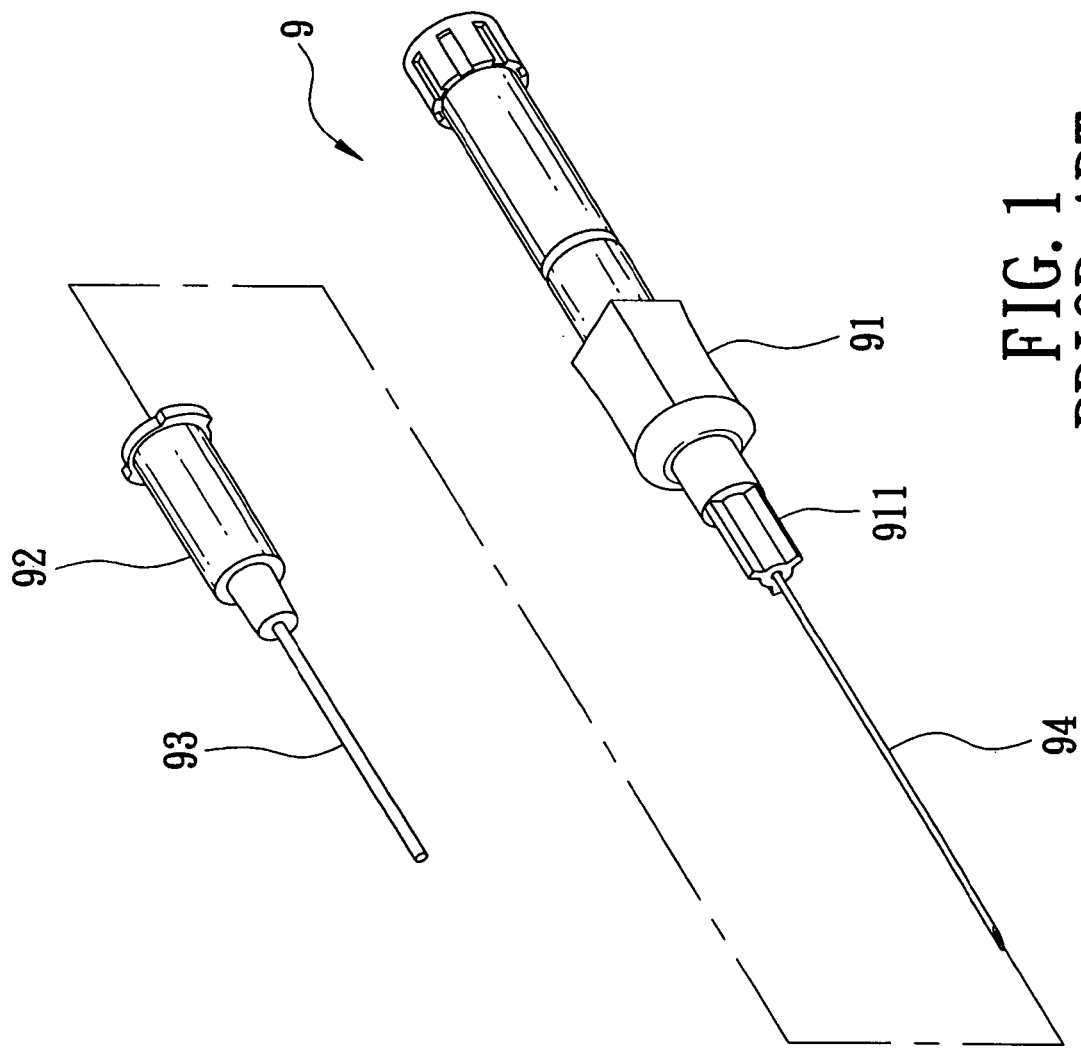
FIG. 1 is a perspective view of a conventional IV catheter introducing device.

Before the present invention is described in greater detail, it should be noted that same reference numerals have been used to denote like elements throughout the specification.

Figure 2:
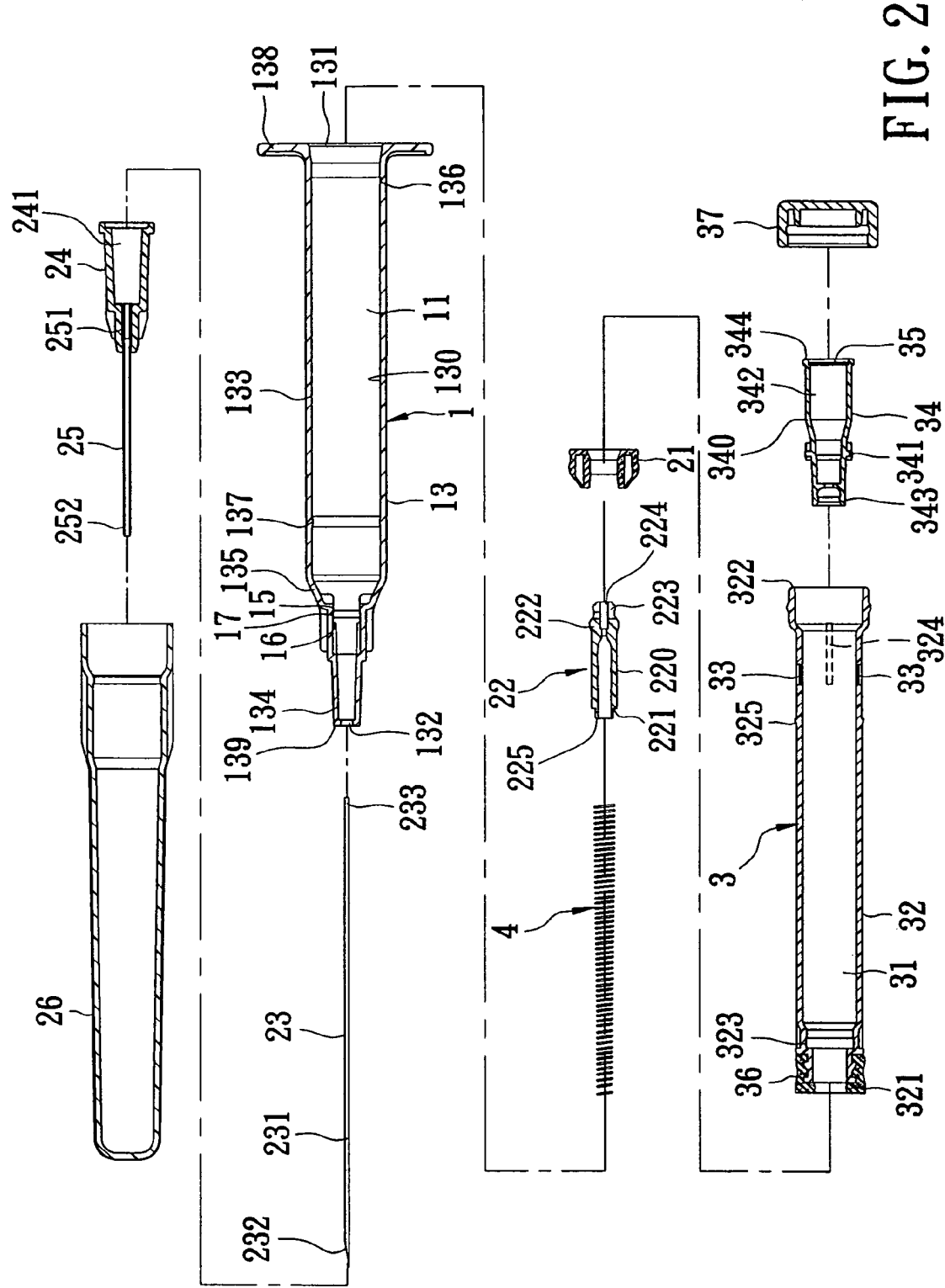
FIG. 2 is an exploded sectional view of a first preferred embodiment of an intravenous catheter introducing device according to this invention.
Figure 3:
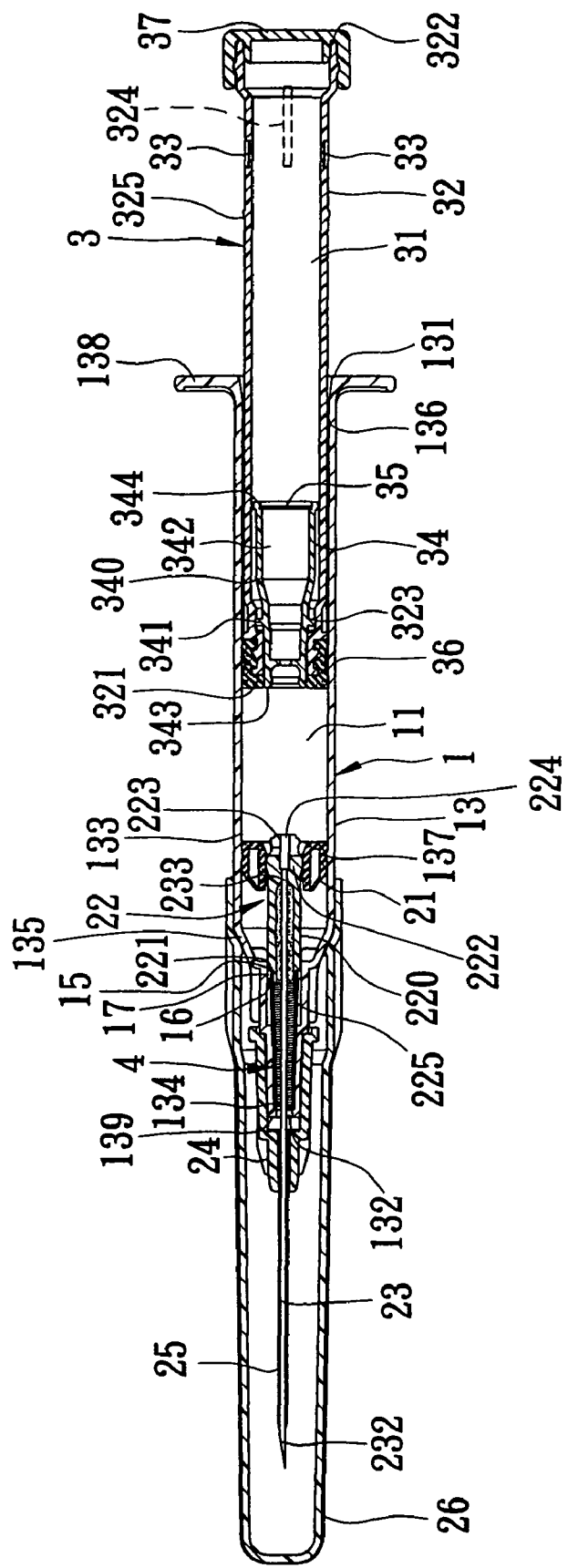
FIG. 3 is a sectional view of the first preferred embodiment in a ready-to-use position.
Figure 4:
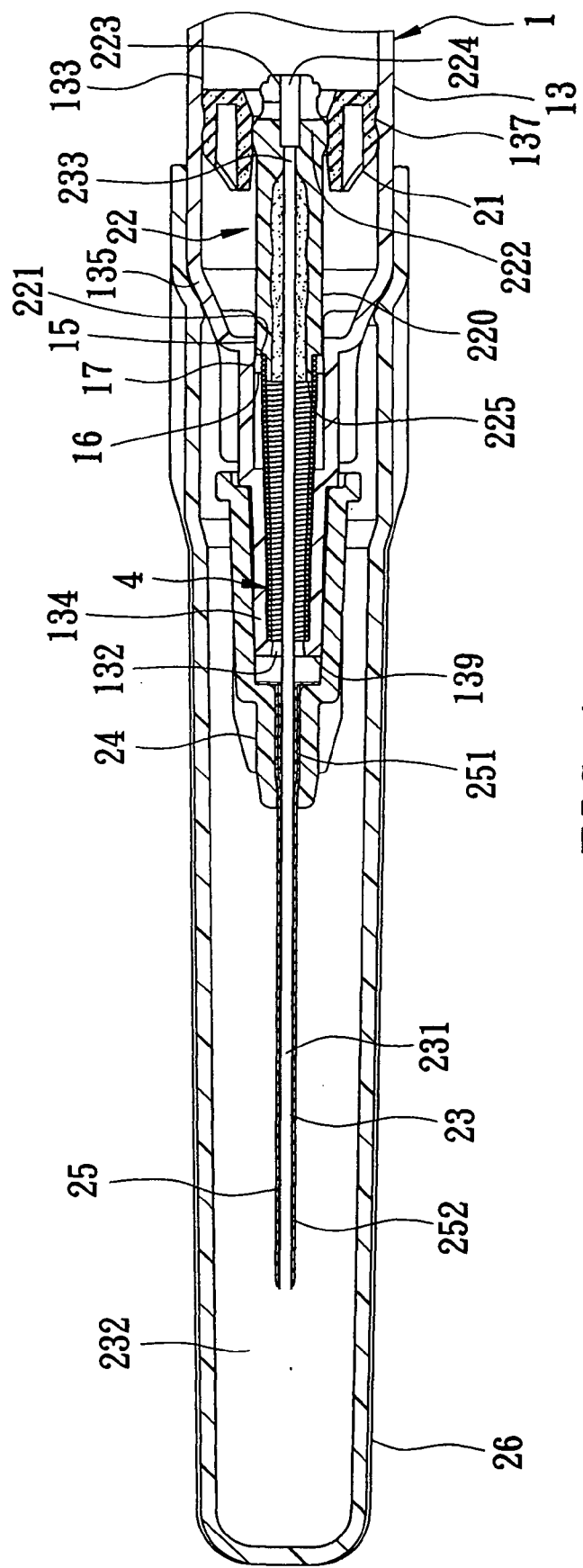
FIG. 4 is a fragmentary sectional view of a portion of the first preferred embodiment.

Referring to FIGS. 2 to 4, the first preferred embodiment of an intravenous catheter introducing device according to the present invention is shown to comprise a barrel 1, a needle cannula 23, a tubular needle seat 22, a tubular grip member 21, a tubular plunger 3, a tubular receptacle 34, a biasing member 4, a catheter hub 24, a tubular catheter 25, and a tip protector 26.

The barrel 1 has a surrounding wall 13 surrounding an axis. The surrounding wall 13 has an inner surrounding barrel surface 130 which defines a passage 11 therein. The passage 11 has rearward and forward openings 131,132 which are opposite to each other in a longitudinal direction along the axis. The inner surrounding barrel surface 130 includes a larger-diameter portion 133 and a smaller-diameter portion 134 which are disposed proximate to the rearward and forward openings 131,132, respectively, and a shoulder 135 which is interposed therebetween. The larger-diameter portion 133 has a projecting retaining area 137 which is spaced apart from the smaller-diameter portion 134 in the longitudinal direction. The smaller-diameter portion 134 includes an entry region 15, a transit region 17 which extends from the entry region 15 forwardly, and an inner annular abutment surface 16 which confronts rearwardly. The barrel 1 further has a finger flange 138 disposed proximate to the rearward opening 131.

The needle cannula 23 has a front segment 231 terminating at a tip end 232, and a rear connecting end 233 opposite to the front segment 231 along the axis.

The tubular needle seat 22 includes a front hub portion 220 which extends along the axis to terminate at a front end 225 to be surrounded by the entry region 15, and which is disposed to fix the rear connecting end 233 of the needle cannula 23 therein, a gripped portion 222 which extends from the front hub portion 220 away from the front end 225, and a rear plug portion 223 which extends from the gripped portion 222 and distal from the front hub portion 220 and which has an internal duct 224 extending through the gripped portion 222 along the axis to be communicated with the rear connecting end 233 of the needle cannula 23. The front hub portion 220 has a shoulder surface 221 which is disposed rearwardly of the front end 225, and which is spaced apart from the inner annular abutment surface 16 by the transit region 17.

The tubular grip member 21 is retained at the retaining area 137 of the barrel 1 in a position of use so as to hold the gripped portion 222 of the needle seat 22 in a position of immovability along the axis relative to the retaining area 137 by virtue of a holding force. To be specific, the tubular grip member 21 is disposed in retaining engagement with the projecting retaining area 137 of the larger-diameter portion 133, and in gripping engagement with the gripped portion 222 of the needle seat 22 by second and third friction forces, respectively, which cooperate in radial directions to serve as the holding force.

The tubular plunger 3 is disposed to be movable in the passage 11 along the larger-diameter portion 130. The plunger 3 has a front opened end wall 321, a rear end wall 322 which is opposite to the front opened end wall 321 and which extends outwardly of the rearward opening 131 so as to be manually operable, and an intermediate surrounding wall 32 which is interposed between the front opened end wall 321 and the rear end wall 322 and which defines an accommodation compartment 31. The intermediate surrounding wall 32 has a plurality of ribs 324 which are formed on an outer surface thereof and adjacent to the rear end wall 322.

The tubular plunger 3 has two outlets 33 which communicate the accommodation compartment 31 with the ambient air, and which are disposed downstream of the air permeable end 344. In this embodiment, the outlets 33 are formed in the intermediate surrounding wall 32 adjacent to the rear end wall 322 to facilitate closing by a user's finger when the user grips and moves the tubular plunger 3.

The tubular plunger 3 further has a deformable sealing member 36 which is configured to surround the front opened end wall 321, and which is in air-tight sliding engagement with the larger-diameter portion 130.

The tubular receptacle 34 has a socket end 343 and an air-permeable end 344 spaced apart from each other in the longitudinal direction, and a tubular wall segment 340 interposed therebetween to confine a flashback chamber 342. In the position of use, the tubular receptacle 34 is retained in the accommodation compartment 31 by a first friction force generated between protrusion and recess portions 341, 323 such that the socket end 343 and the air-permeable end 344 respectively confront the rear plug portion 223 and the rear end wall 322 to establish an air communication between the internal duct 224 and the flashback chamber 342. An air-permeable member 35 is integrally formed with the air-permeable end 344, and is made from a porous material.

The rear end wall 322 of the tubular plunger 3 defines an access opening for insertion of the tubular receptacle 34 into the accommodation compartment 31 therethrough. An end cap 37 is detachably mounted to the rear end wall 322 to close the access opening.

The barrel 1 has a forward end wall 139 which defines the forward opening 132. The biasing member 4 is in the form of a coil spring 4 which surrounds the front segment 231 of the needle cannula 23, and which is compressed between the forward end wall 139 and the shoulder surface 221 of the needle seat 22 to provide a biasing force to move the needle seat 22 rearwardly.

The catheter hub 24 is detachably sleeved on the surrounding wall 13 of the barrel 1, and defines therein a duct 241 that permits extension of the front segment 231 of the needle cannula 23 therethrough.

The tubular catheter 25 has a proximate segment 251 which is inserted into the duct 241, and a distal segment 252 which extends from the proximate segment 251 and which surrounds and sheathes the front segment 231 of the needle cannula 23 while permitting the tip end 232 to project forwardly of the distal segment 252 for piercing a patient's skin.

The tip protector 26 is removably sleeved on the surrounding wall 13 for shielding the needle cannula 23.

In the position of use, the front hub portion 220 of the needle seat 22 is retained at the retaining area 137 by the holding force (i.e., the second and third friction forces), and the inner annular abutment surface 16 is spaced apart from the shoulder surface 221 by the transit region 17.

Figure 5:
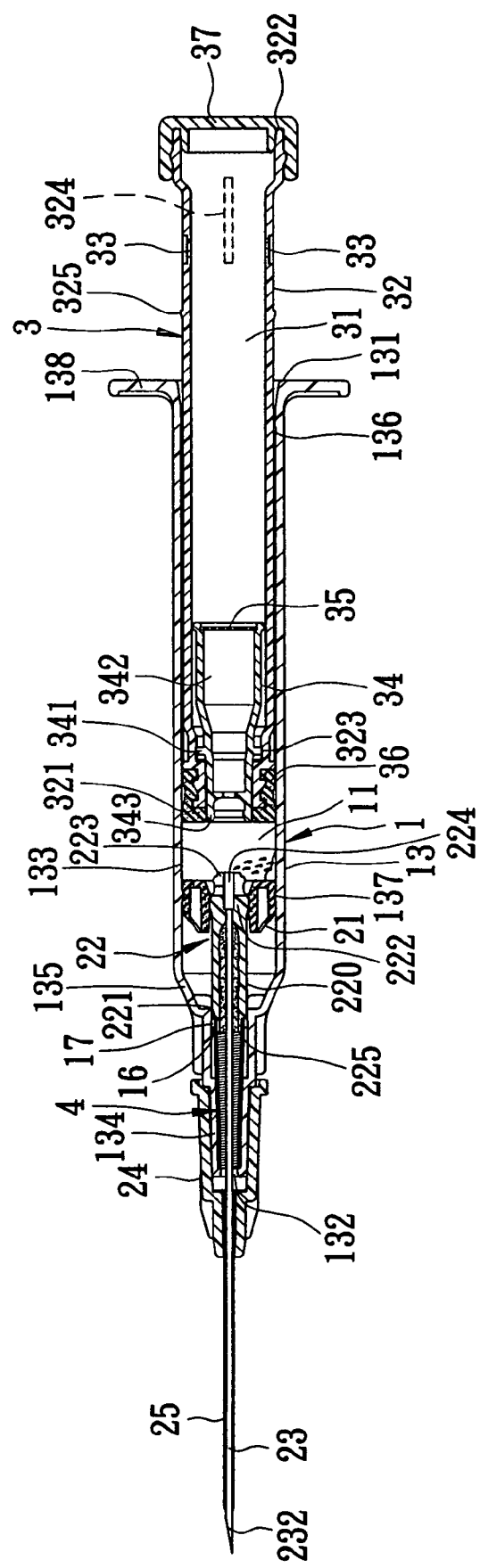
FIG. 5 is a sectional view of the first preferred embodiment in a position of use.

Referring to FIGS. 3, 4 and 5, in an IV introducing stroke, the tip protector 26 is removed first to expose the tip end 232 of the needle cannula 23. The operator grips the surrounding wall 13 of the barrel 1 and pierces the patient's vein with the tip end 232 so as to introduce the tubular catheter 25 into the vein. The blood flowing into the passage 11 is visible from the surrounding wall 13 so that the operator can check whether the needle cannula 23 has been inserted properly into the vein. The operator can then separate the catheter hub 24 from the barrel 1, and the IV introducing operation is completed.

Figure 6:
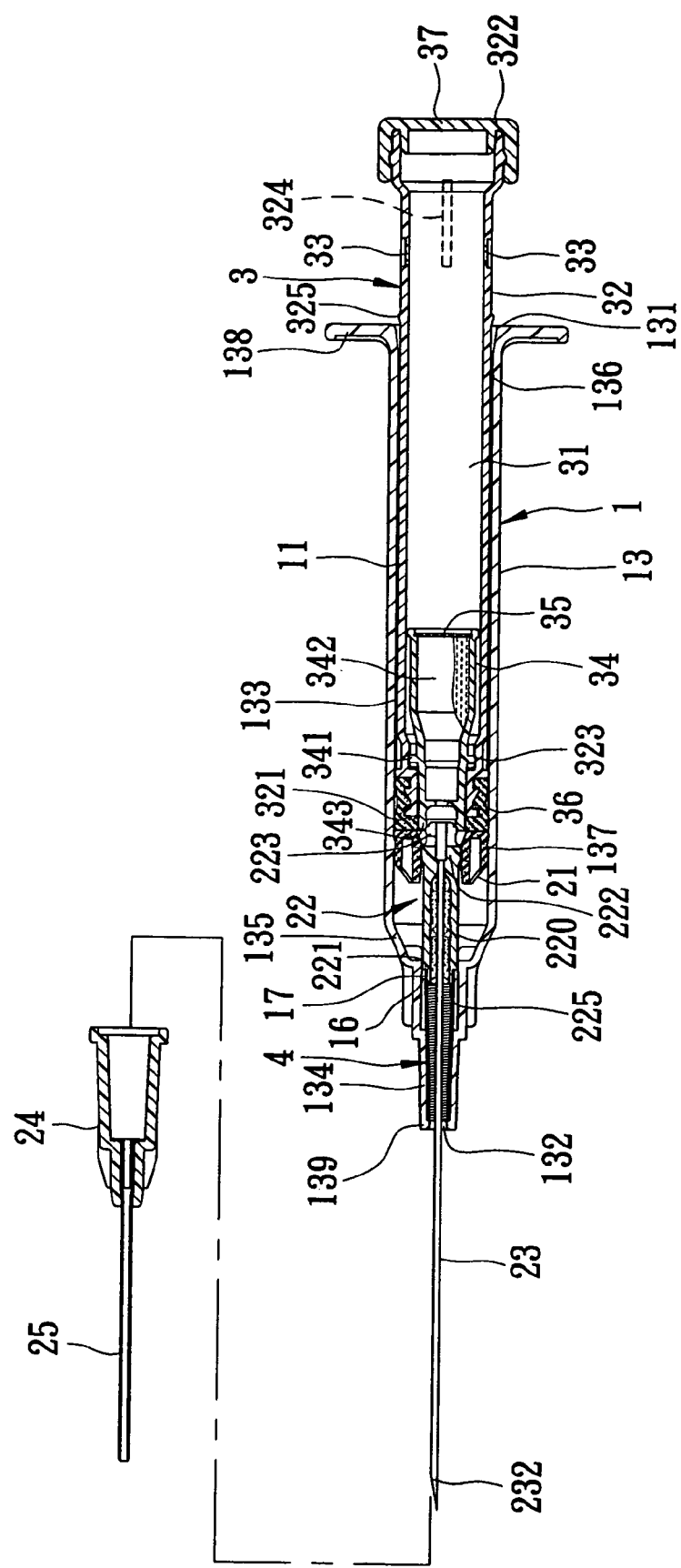
FIG. 6 is a sectional view of the first preferred embodiment in a pre-disposal position.

Referring to FIGS. 5 and 6, since the passage 11 is in air communication with the accommodation compartment 31 via the flashback chamber 342 so as to be communicated with the ambient air through the outlets 33, after the IV introducing stroke, the operator can press the tubular plunger 4 forwardly so as to move the deformable sealing member 36 to abut against the grip member 21 to thereby place the tubular plunger 3 in a pre-disposal position. At this time, the blood in the passage 11 can flow into the flashback chamber 342 due to air communication of the passage 11 with the ambient air, and the air-permeable member 35 can prevent the blood from trickling out of the flashback chamber 342. Thus, the blood will not be forced out of the barrel 1 during forward pressing of the tubular plunger 3.

Subsequently, the socket end 343 is engaged with the rear plug portion 223. When the grip member 21 is pushed forward by virtue of a forward movement of the tubular plunger 3 against the holding force, the grip member 21 is moved to disengage from the retaining region 137 so that the second friction force disappears, and the shoulder surface 221 of the needle seat 22 is moved to pass from the entry region 15 to the transit region 17 to abut against the inner annular abutment surface 16. Then, by virtue of the abutment of the shoulder surface 221 against the inner annular abutment surface 16, the gripped portion 222 is released from the grip member 21 so that the third friction force disappears. The time lag between the releasing of the second and third friction forces can result in a smooth operation of the tubular plunger 3. At the same time, by virtue of a counteracting effect of the forward end wall 139 of the barrel 1 and the coil spring 4, the protrusion portion 341 of the receptacle 34 is moved to disengage from the recess portion 323 in the plunger 3 so as to permit releasing of the coil spring 4.

Figure 7:
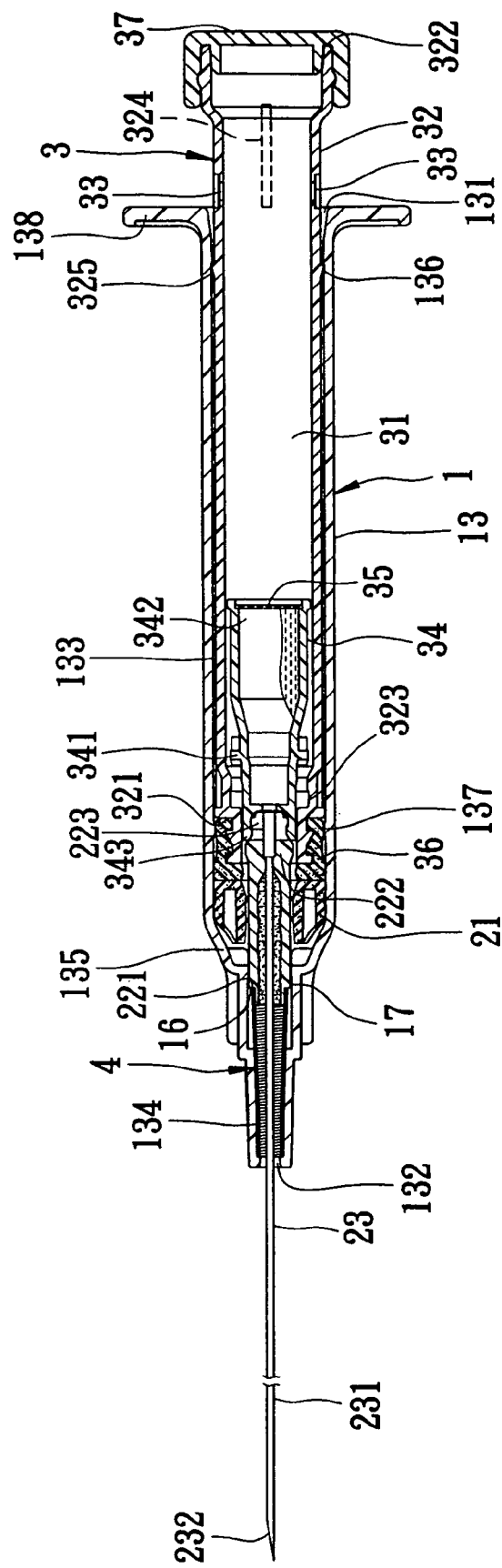
FIG. 7 is a sectional view of the first preferred embodiment during an operation of retracting a needle cannula.
Figure 8:
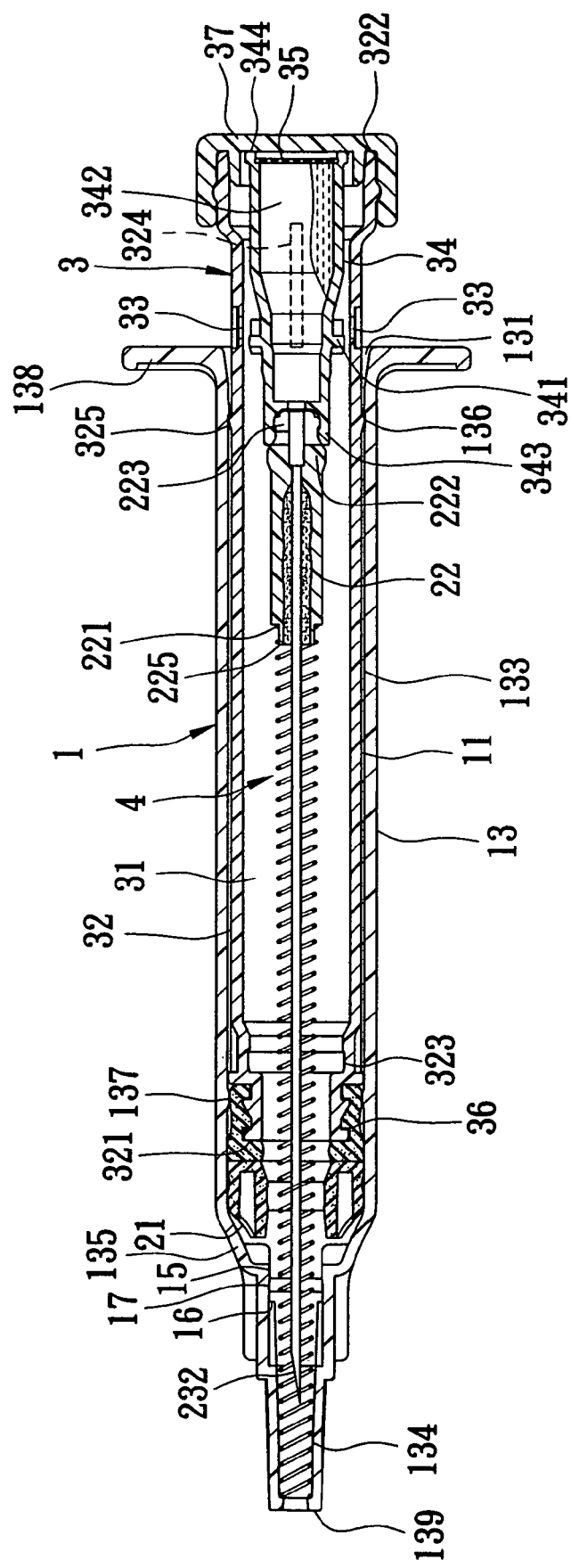
FIG. 8 is a sectional view of the first preferred embodiment in a retracted position.

Therefore, as shown in FIG. 7, through the engagement of the rear plug portion 223 with the socket end 343, a rearward movement of the needle seat 22 will, by virtue of the biasing force of the coil spring 4, force the tubular receptacle 34 to move towards the rear end wall 322 to place the tubular needle seat 22 and the needle cannula 23 in a disposal position, as shown in FIG. 8, where the tip end 232 of the needle cannula 23 is retracted into the passage 11, and where the socket end 343 is closer to the rear end wall 322 than in the position of use.

It is noted that when the tubular plunger 3 is pressed to place the tubular needle seat 22 and the needle cannula 23 in the disposal position, the tubular plunger 3 is retained at the larger-diameter portion 133 through snug engagement between an annular recess 136 and an annular projection 325 so as to prevent rearward pulling of the tubular plunger 3 for reuse. Moreover, the forward pressing of the tubular plunger 3 can be limited by the ribs 324 that abut against the barrel 1 at the rearward opening 131 so as to prevent excess forward movement of the tubular plunger 3, which may cause the grip member 21 to deform and interfere with the rearward movement of the needle seat 22.

Figure 9:
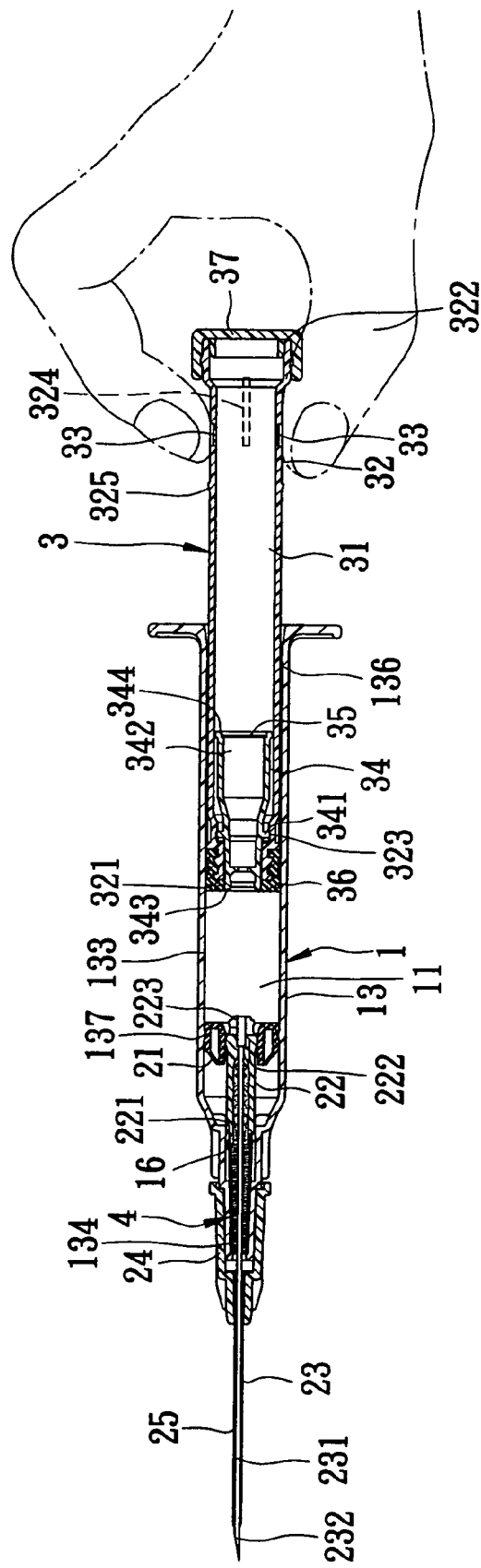
FIG. 9 is a sectional view of the first preferred embodiment showing two outlets in a closed position.

Referring to FIG. 9, during the IV introducing operation, if blood is not observed in the passage 11, the operator can hold the tubular plunger 3 and close the outlets 33 with his/her thumb and index finger to interrupt air communication between the passage 11 and the ambient air. Then the operator can pull the tubular plunger 3 rearwardly so as to generate a reduced pressure in the passage 11 to thereby facilitate flow of blood into the passage 11. Thus, the operator can easily check whether the tubular catheter 25 has been successfully introduced into a target vein of the patient.

Figure 10:
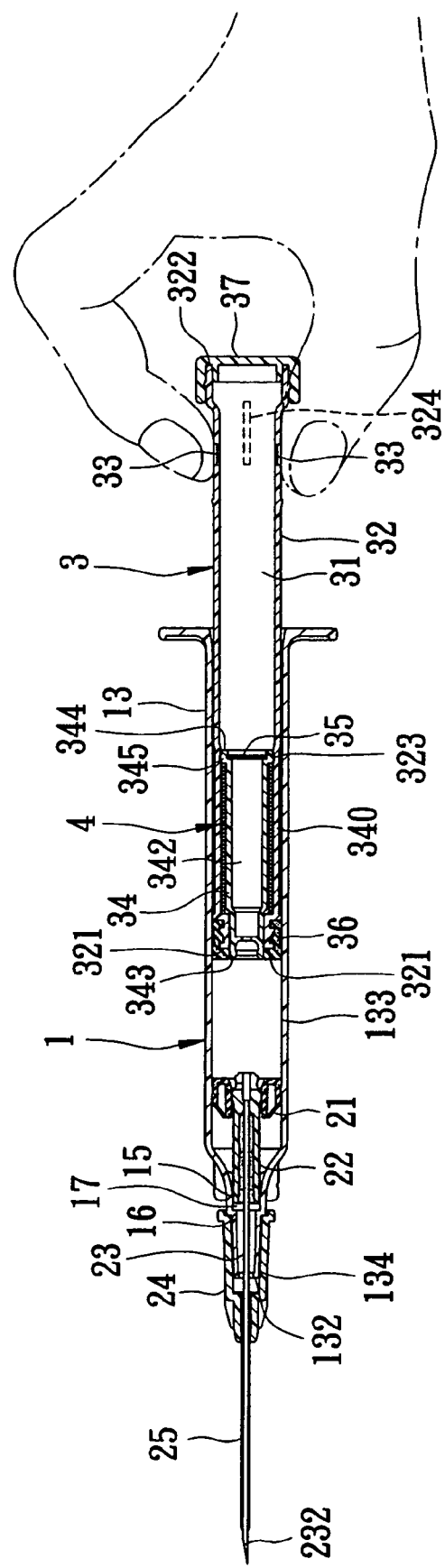
FIG. 10 is a sectional view of the second preferred embodiment of an intravenous catheter introducing device according to this invention.
Figure 11:
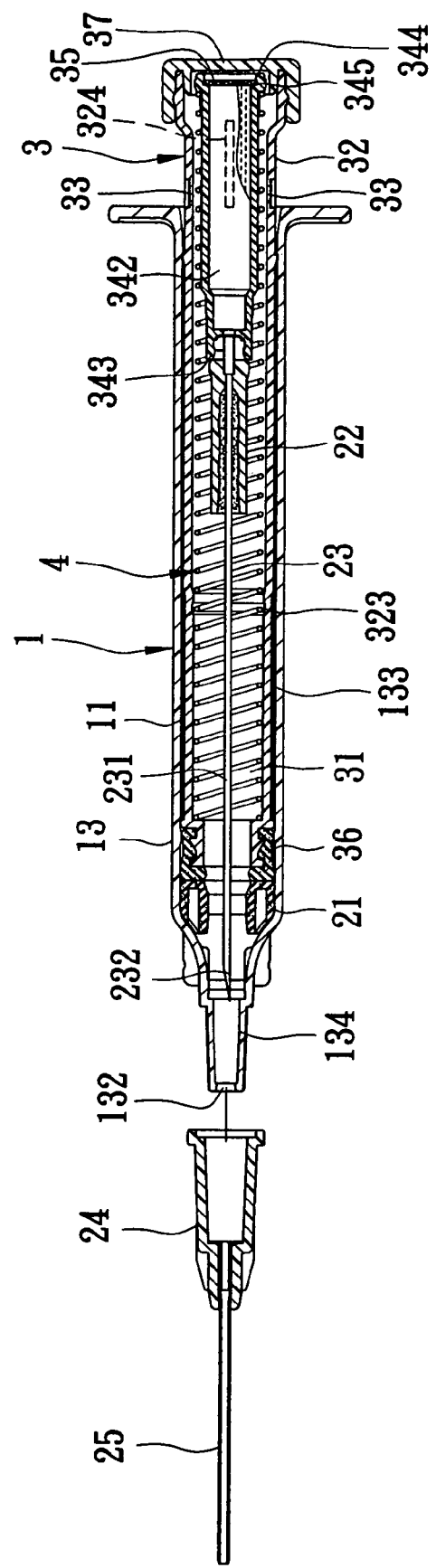
FIG. 11 is a sectional view of the second preferred embodiment in a retracted position.

Referring to FIGS. 10 and 11, the second preferred embodiment of an intravenous catheter introducing device according to this invention is shown to be similar to the first preferred embodiment in construction. The difference resides in that the tubular wall segment 340 of the tubular receptacle 34 has an outer annular abutment surface 345 adjacent to the air-permeable end 344. The biasing member 4 is in the form of a coil spring 4 which surrounds the tubular wall segment 340 and which is compressed between the front opened end wall 321 and the outer annular abutment surface 345. Moreover, the outer annular abutment surface 345 is retained at the recess portion 323 of the tubular plunger 3 to generate the first friction force.

Figure 12:
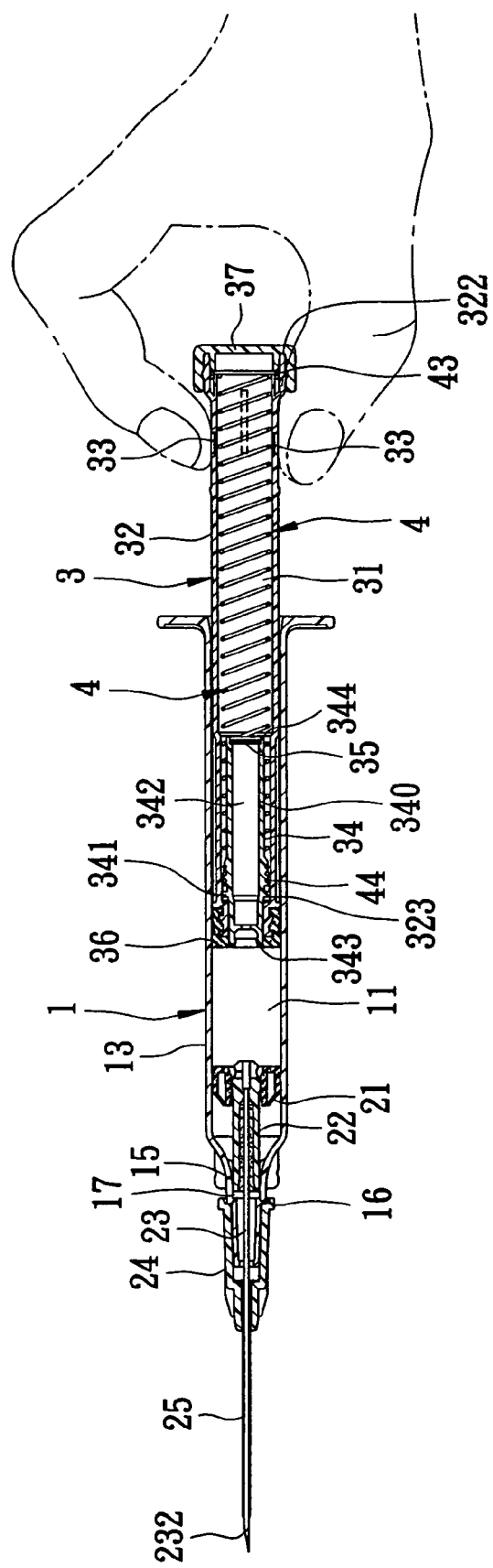
FIG. 12 is a sectional view of the third preferred embodiment of an intravenous catheter introducing device according to this invention.
Figure 13:
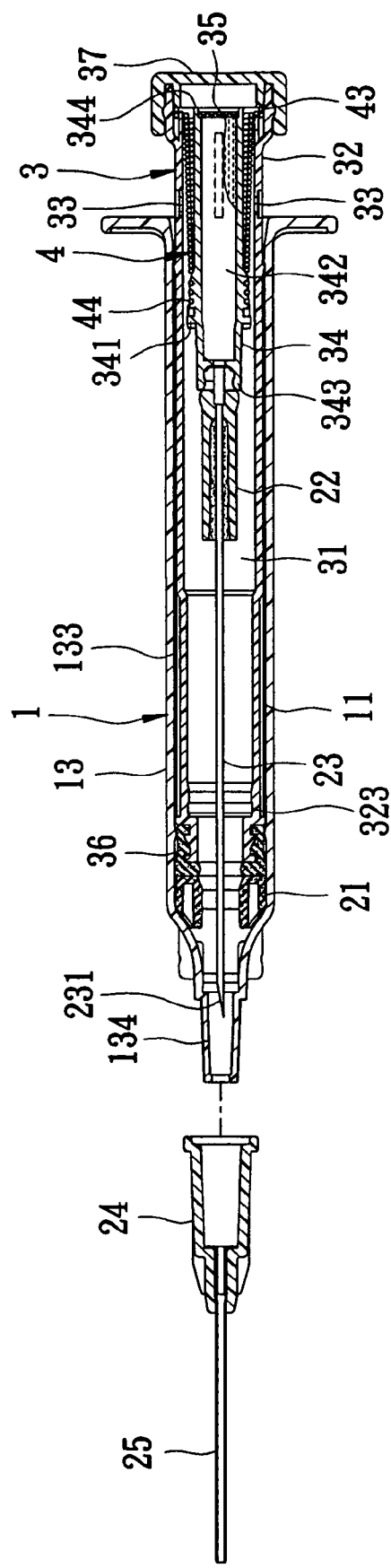
FIG. 13 is a sectional view of the third preferred embodiment in a retracted position.

Referring to FIGS. 12 and 13, the third preferred embodiment of an intravenous catheter introducing device according to this invention is shown to be similar to the first preferred embodiment in construction. The difference resides in that the biasing member 4 is in the form of a coil spring 4 which is received in the accommodation compartment 31 of the tubular plunger 3 and which has a secured end 43 that is secured to the intermediate surrounding wall 32 adjacent to the rear end wall 322, and a tensed end 44 that is secured to the tubular wall segment 340 of the tubular receptacle 34 so as to remain tensed in the position of use.

Figure 14:
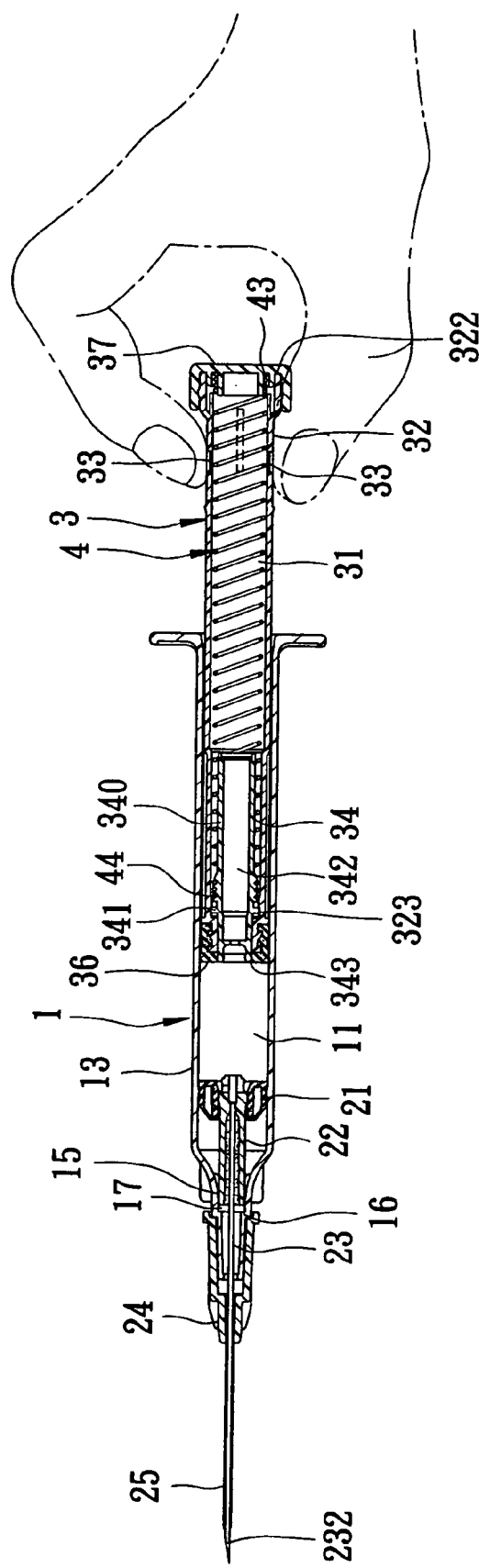
FIGS. 14 to 18 respectively are sectional view of the fourth to eighth preferred embodiments of an intravenous catheter introducing device according to this invention.

Referring to FIG. 14, the fourth preferred embodiment of an intravenous catheter introducing device according to this invention is shown to be similar to the third preferred embodiment in construction. The difference resides in that the biasing member 4 has a secured end 43 which is secured to the end cap 37.

Figure 15:
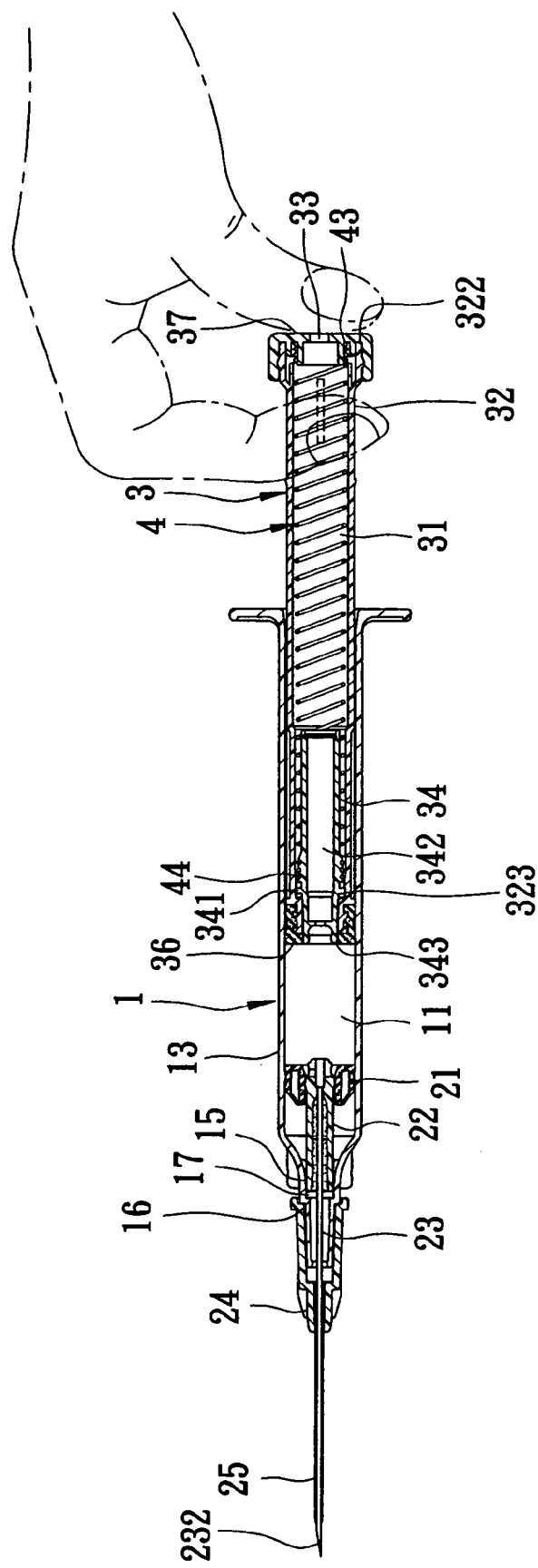

Referring to FIG. 15, the fifth preferred embodiment of an intravenous catheter introducing device according to this invention is shown to be similar to the third preferred embodiment in construction. The difference resides in that the outlet 33 is formed in the end cap 37 to facilitate closing of the outlet 33 by the operator.

Figure 16:
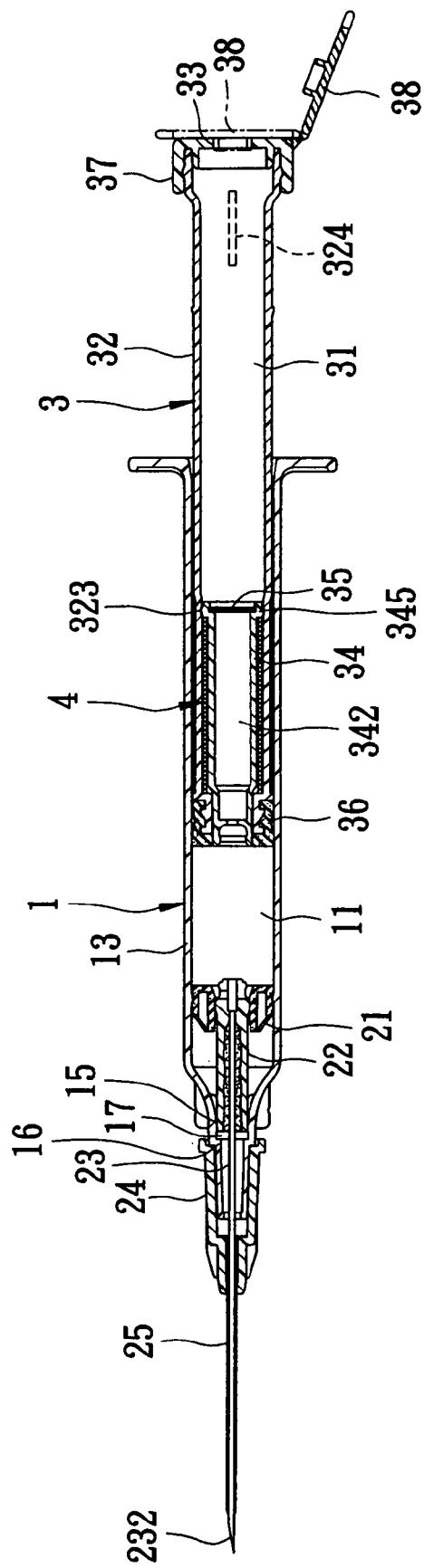

Referring to FIG. 16, the sixth preferred embodiment of an intravenous catheter introducing device according to this invention is shown to be similar to the second preferred embodiment in construction. The difference resides in that the outlet 33 is formed in the end cap 37, and a cover plate 38 is disposed on the tubular plunger 3, and is movable relative to the tubular plunger 3 between closing and opening positions, where the cover plate 38 engages with and disengages from the end cap 37 to close and open the outlet 33, respectively.

Figure 17:
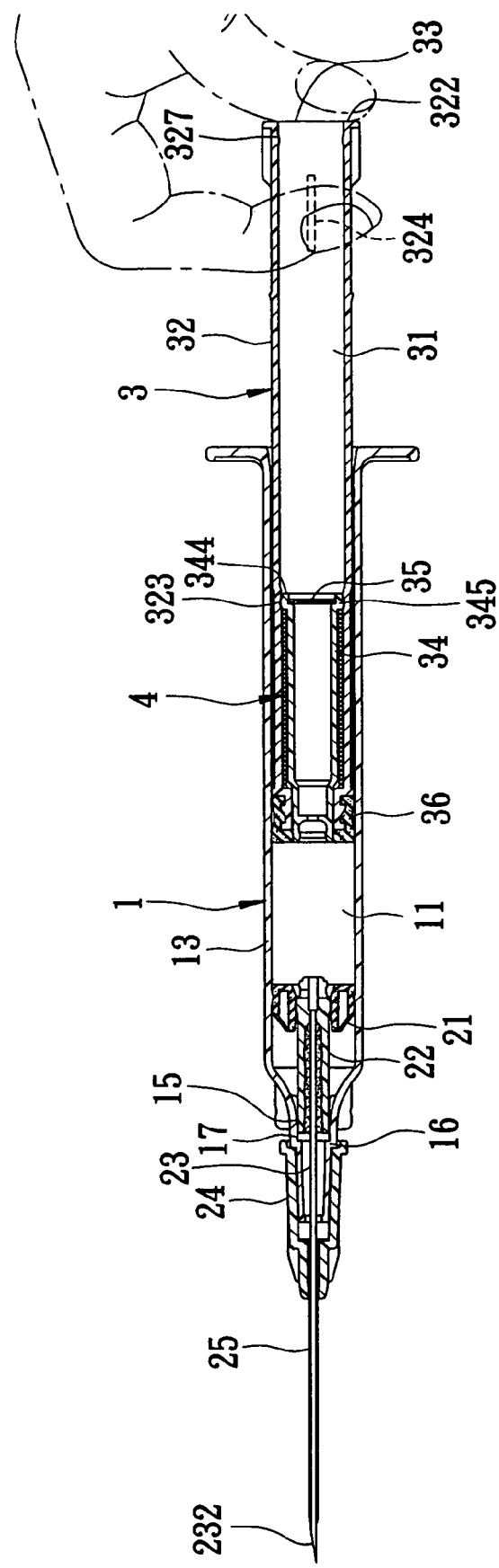

Referring to FIG. 17, the seventh preferred embodiment of an intravenous catheter introducing device according to this invention is shown to be similar to the second preferred embodiment in construction. The difference resides in that the outlet 33 is formed in the rear end wall 322 of the tubular plunger 3, and the intermediate surrounding wall 32 of the tubular plunger 3 has an annular barrier 327 formed adjacent to the rear end wall 322 such that the air-permeable end 344 of the tubular receptacle 34 is stopped by the annular barrier 327 when the tubular receptacle 34 is moved to the disposal position.

Figure 18:
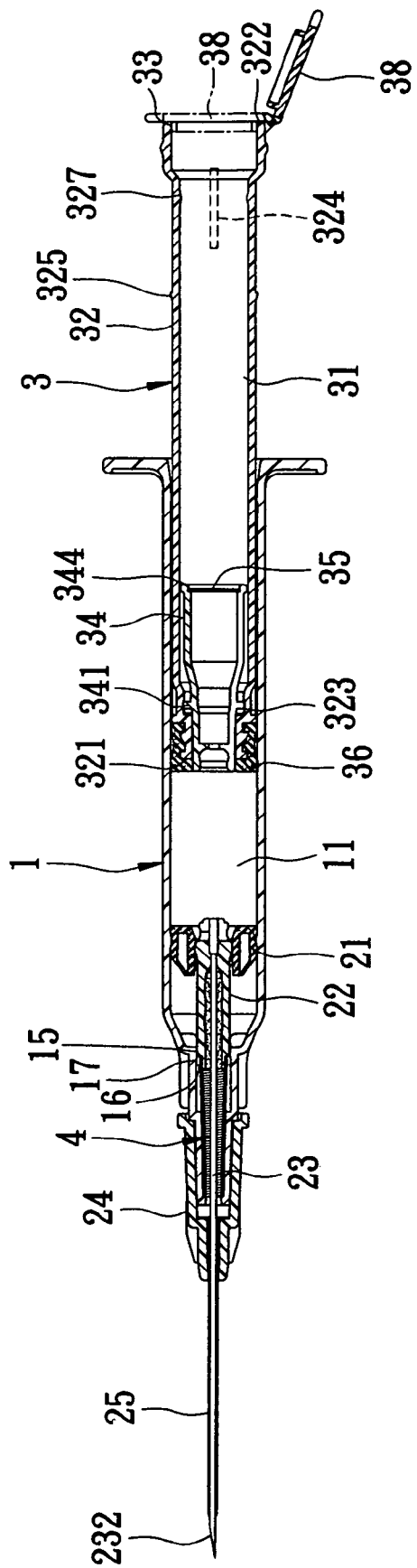

Referring to FIG. 18, the eighth preferred embodiment of an intravenous catheter introducing device according to this invention is shown to be similar to the first preferred embodiment in construction. The difference resides in that the outlet 33 is formed in the rear end wall 322 of the tubular plunger 3, and the intermediate surrounding wall 32 of the tubular plunger 3 has an annular barrier 327 formed adjacent to the rear end wall 322 such that the air-permeable end 344 of the tubular receptacle 34 is stopped by the annular barrier 327 when the tubular receptacle 34 is moved to the disposal position. In addition, a cover plate 38 is disposed on the tubular plunger 3 and is movable relative to the tubular plunger 3 between closing and opening positions, where the cover plate 38 engages and disengages from the rear end wall 322 to close and open the outlet 33, respectively.

As illustrated, according to the intravenous catheter introducing device of this invention, the used needle cannula 23 can be retracted into the passage 11 of the barrel 1 to thereby avoid occurrence of an accidental needle stick. Further, during the forward pressing of the tubular plunger 3 to retract the needle cannula 23, since the passage 11 is air communicated with the ambient air, the blood in the passage 11 may flow into the flashback chamber 342, and the air-permeable member 35 can prevent the blood from trickling out of the flashback chamber 342. Thus, the blood will not be forced out of the barrel 1. Moreover, during the IV introducing operation, once blood is not observed in the passage 11, the operator can close the outlet(s) 33 and pull the tubular plunger 3 rearwardly to generate a reduced pressure in the passage 11 to thereby facilitate flow of blood into the passage 11. Thus, the operator can easily check whether the tubular catheter 25 has been successfully introduced into a target vein of the patient.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We claim:

1. An intravenous catheter introducing device comprising:

a needle cannula having a front segment terminating at a tip end, and a rear connecting end opposite to said front segment along the axis in a longitudinal direction;

a tubular needle seat which includes a front hub portion that extends along the axis to terminate at a front end, and that is disposed to fix said rear connecting end therein, a gripped portion that extends from said front hub portion away from said front end, and a rear plug portion that extends from said gripped portion and distal from said front hub portion, and that has an internal duct extending through said gripped portion along the axis to be communicated with said rear connecting end;

a barrel having an inner surrounding barrel surface which surrounds the axis, and which defines a passage therein, said passage having rearward and forward openings which are opposite to each other in the longitudinal direction, said inner surrounding barrel surface including a larger-diameter portion and a smaller-diameter portion which are disposed proximate to said rearward and forward openings, respectively, said larger-diameter portion having a retaining area which is spaced apart from said smaller-diameter portion in the longitudinal direction;

a tubular grip member which, in a position of use, is disposed to hold, with a holding force, said gripped portion in a position of immovability along the axis relative to said retaining area;

a tubular plunger which is disposed to be movable in said passage along said larger-diameter portion, said plunger having a front opened end wall which is movable to abut against said grip member so as to place said tubular plunger in a pre-disposal position, a rear end wall which is disposed opposite to said front opened end wall, and which extends outwardly of said rearward opening so as to be manually operable, and an intermediate surrounding wall which is interposed between said front opened end wall and said rear end wall, and which defines an accommodation compartment;

a tubular receptacle which has a socket end and an air-permeable end spaced apart from each other in the longitudinal direction, and a tubular wall segment interposed between said socket end and said air-permeable end to confine a flashback chamber, wherein, when said tubular grip member is in the position of use, said tubular receptacle is retained in said accommodation compartment by a first friction force, with said socket end and said air-permeable end respectively confronting said rear plug portion and said rear end wall to establish air communication between said internal duct and said flashback chamber, such that when said tubular plunger is in the pre-disposal position, said socket end is engaged with said rear plug portion, such that when said grip member is pushed forward by virtue of a forward movement of said front opened end wall against the holding force, said gripped portion is released from said grip member to permit axial movement of said gripped portion relative to said retaining area, and such that when said gripped portion is released from said grip member, a continued forward movement of said front opened end wall against the first friction force will result in movement of said needle seat together with said tubular receptacle, through the engagement of said rear plug portion with said socket end, towards said rear end wall by virtue of a biasing force so as to place said needle seat and said needle cannula in a disposal position, where said tip end of said needle cannula is retracted into said passage, and where said socket end is closer to said rear end wall than in the position of use; and a biasing member disposed to provide said biasing force.

2. The intravenous catheter introducing device of claim 1, wherein said smaller-diameter portion includes an entry region which is configured to surround said front hub portion, and a transit region which extends from said entry region towards said forward opening, said tubular grip member being disposed to be in retaining engagement with said retaining area of said larger-diameter portion, and in gripping engagement with said gripped portion of said needle seat by second and third friction forces, respectively, which cooperate in radial directions to serve as the holding force, such that once an axial movement of said gripped portion commences relative to said retaining area by virtue of the forward movement of said grip member and said front opened end wall, said front hub portion is moved to pass from said entry region to said transit region so as to permit said tubular grip member to be disengaged from said retaining area before disengagement of said gripped portion from said tubular grip member in the pre-disposal position.

3. The intravenous catheter introducing device of claim 2, wherein said front hub portion of said needle seat has a shoulder surface which is disposed rearwardly of said front end, and which faces towards said forward opening, said smaller-diameter portion further including an inner annular abutment surface which is spaced apart from said shoulder surface by said transit region such that by virtue of abutment of said shoulder surface against said inner annular abutment surface, forward movement of said grip member and said front opened end wall results in release of said gripped portion from said grip member against the third friction force.

4. The intravenous catheter introducing device of claim 3, wherein said barrel has a forward end wall which defines said forward opening, said biasing member being in the form of a coil spring which surrounds said front segment of said needle cannula, and which is compressed between said forward end wall and said shoulder surface of said needle seat.

5. The intravenous catheter introducing device of claim 1, further comprising an air-permeable member which is made from a porous material, and which is integrally formed with said air-permeable end so as to prevent blood from trickling out of said flashback chamber.

6. The intravenous catheter introducing device of claim 1, wherein said tubular plunger has a deformable sealing member which is configured to surround said front opened end wall, and which is in air-tight sliding engagement with said larger-diameter portion.

7. The intravenous catheter introducing device of claim 1, wherein said tubular plunger has an outlet that communicates said accommodation compartment with the ambient air, and that is disposed downstream of said air permeable end.

8. The intravenous catheter introducing device of claim 7, wherein said outlet is formed in said intermediate surrounding wall adjacent to said rear end wall to facilitate closing by a user's finger when the user grips and moves said tubular plunger.

9. The intravenous catheter introducing device of claim 1, further comprising:
a catheter hub which defines therein a duct that permits extension of said front segment of said needle cannula therethrough; and
a tubular catheter having a proximate segment which is inserted into said duct, and a distal segment which extends from said proximate segment and which surrounds and sheathes said front segment of said needle cannula while permitting said tip end to project forwardly of said distal segment for piercing a patient's skin.

10. The intravenous catheter introducing device of claim 1, wherein said tubular plunger and said larger-diameter portion respectively have an annular projection and an annular recess which are configured such that once said tubular plunger is placed in the pre-disposal position, said annular projection and said annular recess are snugly engaged with each other so as to prevent rearward pulling of said tubular plunger for reuse.

11. The intravenous catheter introducing device of claim 1, wherein said intermediate surrounding wall of said tubular plunger has a plurality of ribs which are formed on an outer surface thereof and adjacent to said rear end wall and which are disposed to abut against said barrel at said rearward opening when said tubular plunger is in the disposal position.

* * * * *